(12) United States Patent
Pop et al.

(10) Patent No.: US 7,132,651 B2
(45) Date of Patent: Nov. 7, 2006

(54) IN-SITU BWR AND PWR CRUD FLAKE ANALYSIS METHOD AND TOOL

(75) Inventors: Mihai G. M. Pop, Lynchburg, VA (US); Brian G. Lockamon, Evington, VA (US); Laurence S. Lamanna, Amherst, VA (US); John T. Willse, Lynchburg, VA (US)

(73) Assignee: Framatome ANP, Inc., Lynchburg, VA (US)

( * ) Notice: Subject to any disclaimer, the term of this patent is extended or adjusted under 35 U.S.C. 154(b) by 250 days.

(21) Appl. No.: 10/830,913

(22) Filed: Apr. 23, 2004

(65) Prior Publication Data

US 2006/0227922 A1    Oct. 12, 2006

(51) Int. Cl.
*G01N 23/225*    (2006.01)
(52) U.S. Cl. ...................................... 250/307
(58) Field of Classification Search .............. None
See application file for complete search history.

(56) References Cited

U.S. PATENT DOCUMENTS

| | | | |
|---|---|---|---|
| 4,483,205 A | 11/1984 | Bellaiche et al. | |
| 4,662,231 A | 5/1987 | Schaarschmidt et al. | |
| 4,847,042 A | 7/1989 | Musiol et al. | |
| 5,046,289 A | 9/1991 | Bengel et al. | |
| 5,838,752 A | 11/1998 | Shimamura | |
| 6,064,708 A | 5/2000 | Sakamaki | |
| 6,466,637 B1 | 10/2002 | Bowen et al. | |
| 6,504,077 B1 * | 1/2003 | Purohit et al. | 588/18 |
| 6,813,329 B1 * | 11/2004 | Byers et al. | 376/454 |
| 2005/0045564 A1 * | 3/2005 | Akay et al. | 210/708 |

* cited by examiner

*Primary Examiner*—Jack I. Berman
(74) *Attorney, Agent, or Firm*—Kenyon & Kenyon LLP

(57) ABSTRACT

The invention provides a method and tool to perform an analysis of CRUD on a nuclear fuel rod. The method recites providing a nuclear fuel rod with a layer of CRUD on an exterior of the fuel rod, scraping the CRUD from the fuel rod with a CRUD scraping tool and collecting CRUD flakes from the CRUD scraping tool. The method also provides for sorting the CRUD flakes into particle fractions, and analyzing the CRUD with a scanning electron microscope, wherein the scraping tool has a blade with a rigidity that is matched to an anticipated CRUD deposit shear strength.

6 Claims, 13 Drawing Sheets

IN-SITU BWR AND PWR CRUD FLAKE ANALYSIS METHOD AND TOOL

FIELD OF THE INVENTION

The current invention relates to a CRUD analysis method and tool. More specifically, the current invention provides a CRUD analysis methodology and a scraping tool for nuclear fuel rods to determine physical properties of CRUD deposited on an exterior of a nuclear fuel rod.

BACKGROUND INFORMATION

Nuclear reactors, such as pressurized water reactors and boiling water reactors, generate nuclear power through the use of nuclear fuel assemblies housed in a reactor core. The fuel assemblies are comprised of elongated hollow metallic tubular fuel rods that contain pellets of enriched uranium dioxide material. The hollow metallic fuel tubular rods, commonly known in the nuclear industry as cladding, prevent the escape of materials, such as uranium dioxide and fission gasses, from the interior of the fuel rod. The cladding is generally configured from an alloy of differing metals including zirconium. These alloys are used principally because of the low neutron capture characteristic of zirconium. As a consequence of the low neutron capture characteristic, these alloys have been used extensively in the nuclear industry as the nuclear reaction in the reactor is least hindered by such use.

Fuel rods that have been irradiated and have had the enriched uranium dioxide content depleted due to operation of the reactor core, are often stored in pools of cooling water to remove decay heat. As time passes, materials can collect on an exterior surface of the zirconium based alloys. Moreover, the zirconium alloy may warp and swell on the exterior portion of the fuel rod, creating a further layer of material on the underlying sound zirconium alloy substrate. The material which collects on the exterior of the zirconium based alloy is commonly known as Chalk River Unidentified Deposit or "CRUD." The CRUD located on an exterior of the fuel rods of a fuel assembly is generally made of solid particles, agglomerated together, that can be strongly attached to the underlying substrate. Due to the closeness of the CRUD to the activated uranium dioxide material in the fuel assemblies, the CRUD is usually highly radioactive. The CRUD on the fuel rods can become dislodged from the underlying zirconium alloy substrate by flowing water that the fuel assemblies are immersed in. Consequently, CRUD can enter the piping of the water systems in the nuclear power plant and travel along these systems causing unintended irradiation of personnel in plant areas that are normally not radiologically active.

Although CRUD is a non-homogenous material, CRUD has been found to be generally made of several elemental components. The major components of CRUD can include, for example, iron, cobalt, zinc, silica, chrome and manganese. As nuclear plant fuel performance is influenced by CRUD deposition during normal plant operation as well as sequence and economics of refueling and maintenance outages, it is necessary to analyze fuel assemblies for the presence of CRUD to determine the nature and amount of the deposits. For example, if it is determined that the nuclear fuel rods have a highly radioactive CRUD layer that may become easily dislodged, then a worker radiological concern exists where the fuel rods may be required to be cleaned. This cleaning process is usually conducted by a number of means, ultrasonically or chemically cleaning the exterior of the fuel rods to remove the loose CRUD buildup.

To perform analysis of crud deposited on the fuel assemblies, samples must be taken by mechanically scraping the exterior of the fuel rods. The systems used to perform this mechanical scraping include a rigid member that the fuel rod is pressed against, thereby shearing the loose CRUD from the rest of the nuclear fuel rod when the fuel rod is moved over the rigid member.

Devices for mechanical scraping fuel rods may be divided into two sub-classes. Manually operated devices may be used to remove the CRUD from the exterior surface of the nuclear fuel rods. Such devices consist of a scraping head at the end of a shaft, wherein the scraping head is used to dislodge loose CRUD from the exterior surface of the fuel rod. Automated devices may also be used to remove deposits from irradiated fuel rods. The fuel rods are scraped by a remote control scraping device, wherein the scraped sample is conveyed to an internal reservoir.

Previous devices of both sub-categories have several drawbacks that limit the effectiveness of the removal devices. Existing manual devices are only used to remove materials from an outside of a fuel rod that are easily dislodgable. CRUD deposits that are attached to the nuclear fuel rod more tenaciously are not able to be removed using existing manual tools. As a result, the manual tools used do not provide an accurate representation of CRUD materials that may be present in the entire depth of the fuel rod as the sampling occurs only on an exterior subsection of the total CRUD deposit. Mechanized devices, however, scrape the nuclear fuel rods such that the entire CRUD deposit is removed from a portion of the fuel rod surface, as well as warped zirconium alloy on the external portion of the nuclear fuel rod. Removal of any warped zirconium alloy on an external portion of the nuclear fuel rod damages the fuel rod. This necessitates an extensive engineering analysis to determine if the pressure retaining capabilities of the fuel rod have been severely compromised. When the material constituents of the exterior of the fuel rod are sampled after using a mechanized device, zirconium alloy inappropriately removed from the rod will skew the material analysis results. Another drawback of existing mechanized devices for removing CRUD deposits on the exterior of fuel rods is that these devices are economically expensive to produce and often require significant maintenance for operation. Additionally, performing maintenance activities on radioactive components of the mechanized devices increases worker radiation exposure.

There is therefore a need to provide a CRUD removal tool, which is cost effective for nuclear reactor operators.

There is also a need for a CRUD removal tool, which will limit potential damage to nuclear fuel rods during removal of CRUD.

There is also a need for an analysis method for CRUD deposits, which will adequately categorize CRUD obtained from scraped fuel rods.

SUMMARY

The objectives of the invention are achieved as described and illustrated. The invention provides a method to perform an analysis of CRUD on a nuclear fuel rod. The method recites providing a nuclear fuel rod with a layer of CRUD on an exterior of the fuel rod, scraping the CRUD from the fuel rod with a CRUD scraping tool and collecting CRUD flakes from the CRUD scraping tool. The method also provides for sorting the CRUD flakes into particle fractions, and analyzing the CRUD with a number of analytical tools including a scanning electron microscope, wherein the scraping tool has a blade with a rigidity that is matched to an anticipated CRUD deposit shear strength.

The invention further provides a method to perform an analysis of a CRUD flake on a nuclear fuel rod. The method provides providing an electron backscattered pattern apparatus to a scanning electron microscope; and otherwise actuating the scanning electron microscope apparatus to determine a crystal system, lattice parameter of unit cells and a point of group crystals belonging to an in-situ portion of the flake.

The invention further provides a method for analysis of a CRUD flake cross section on a nuclear fuel rod. This method recites determining a morphology of crystals of the flake, determining a size of the crystals of the flake, correlating elemental distributions of the flake at various locations on the flake, wherein the distributions are obtained with a scanning electron microscope with attached energy dispersive spectrometer, determining for example a depletion of iron enrichment- and/or an enrichment in zinc and silicon in the crystals by the elemental distributions, and correlating the depletion of iron enrichment and the enrichment in zinc and silicon with the size and the morphology of the crystals.

The invention also provides a method for analysis of a CRUD flake cross section on a nuclear fuel rod. The invention provides the steps of determining a morphology of crystals of the flake, determining a size of the crystals of the flake, correlating elemental distributions of the flake at various locations on the flake, wherein the distributions are obtained with a scanning electron microscope with attached energy dispersive spectrometer, determining a depletion of iron enrichment and an enrichment in zinc and silicon in the crystals by the elemental distributions, and correlating the depletion of iron enrichment and the enrichment in zinc and silicon with the size and the morphology of the crystals.

DETAILED DESCRIPTION

Figure 1:
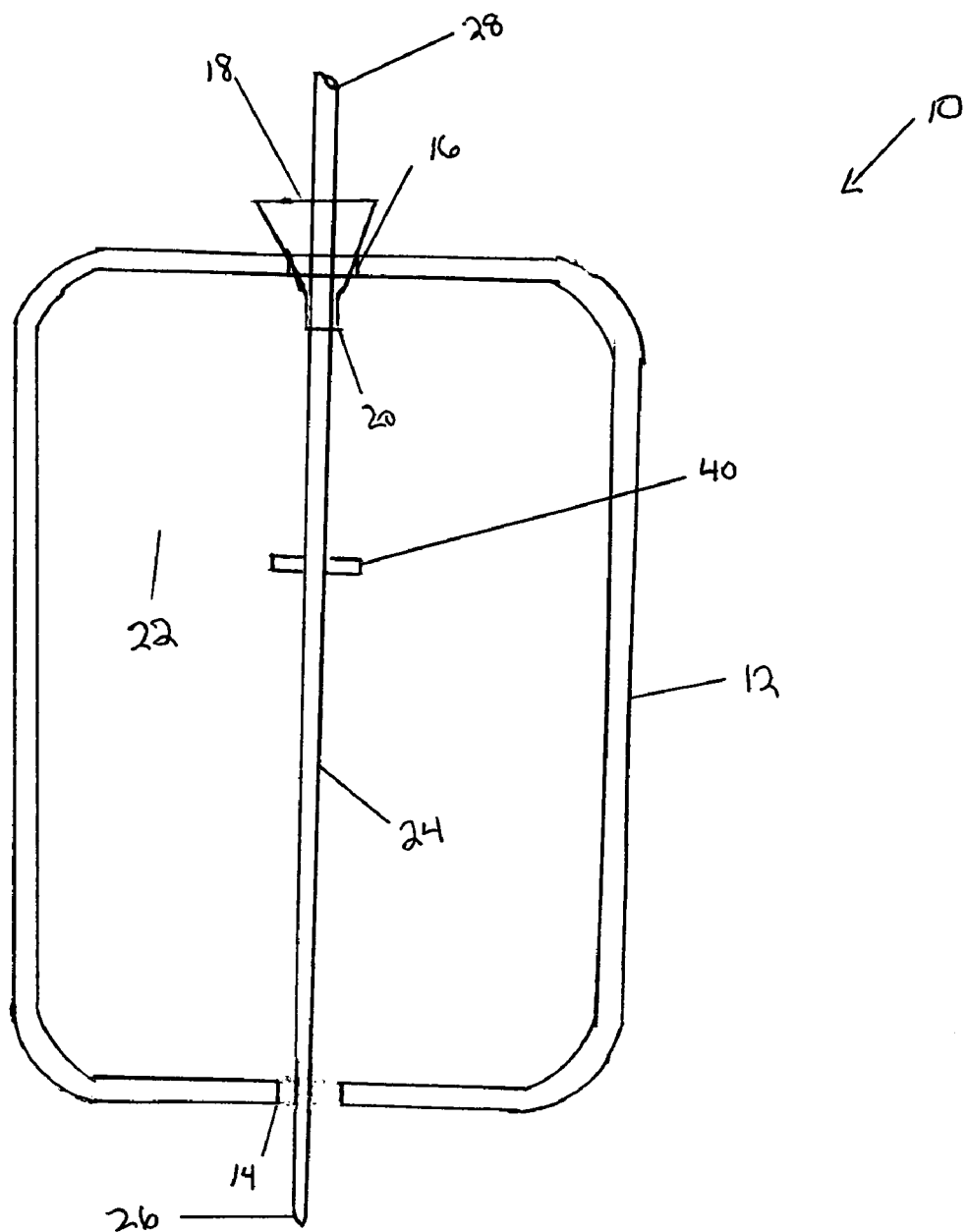
FIG. 1 is a plan view of a fuel rod scraping tool in conformance with an example embodiment of the present invention.

Referring to FIG. 1, a CRUD removal device 10 is illustrated. The CRUD removal device 10 allows CRUD to be removed from an exterior of a nuclear fuel rod 24 in a safe and controlled environment. The CRUD removal device 10 allows the CRUD to be removed in a nuclear fuel pool of a nuclear facility, for example, such that loose or firmly attached CRUD may be dislodged. The CRUD removal device 10 further allows the CRUD to be dislodged without removing warped zircalloy material from the stabilized zircalloy substrate. The device 10 may be made of materials, such as stainless steel, to hinder potential corrosion. A blade 40 is placed in the CRUD removal device 10 such that the fuel rod 24 runs over the blade 40 to facilitate removal of the CRUD layer. Although shown as a single blade 40, multiple blades may be used. A housing 12 defines an interior volume 22 which allows the fuel rod 24 to be partially contained within the housing 12. The fuel rod 24 penetrates the housing 12 through a funnel weldment 18 which is placed into a funnel weldment opening 16 of the housing 12. The fuel rod 24 extends from a fuel rod upper end 28 to a fuel rod end 26, wherein sections of the fuel rod 24 between the fuel rod upper end 28 and the fuel rod end 26 maybe passed through the housing 12 during scraping operations when the rod is translated through the housing 12.

Figure 2:
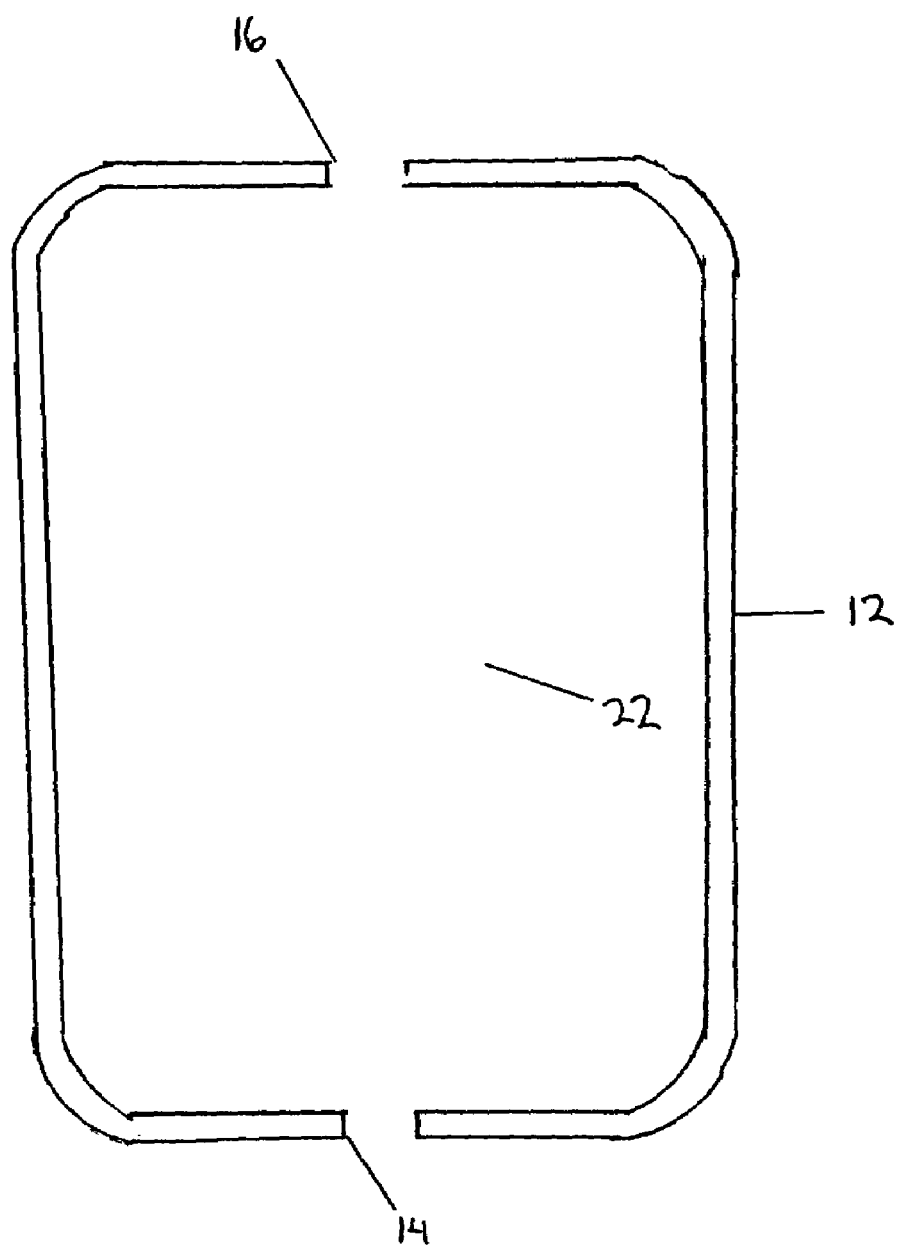
FIG. 2 is a plan view of a tool housing of FIG. 1.

Referring to FIG. 2, the funnel weldment opening 16 and an end opening 14 in the housing of 12 are further illustrated. The end opening 14 may be configured with a rod seal such that when a fuel rod 24 is placed in the housing 12 and the fuel rod 24 extends out of the housing 12, the rod seal prevents any materials inside the housing 12 from escaping out of the housing 12 through the opening 14. Alternatively, the end opening 14 may be sized to snuggly fit around a fuel rod 24, thereby preventing material from escaping the housing 12. The housing 12 is configured such that any volume of CRUD may be confined by the components of the housing 12, including multiple scrapings of several fuel rods 24. In an example embodiment, the housing 12 is configured such that an anticipated volume of CRUD dislodged from the fuel rod 24 may be sufficiently housed in the interior volume 22 defined by the housing 12.

Figure 3:
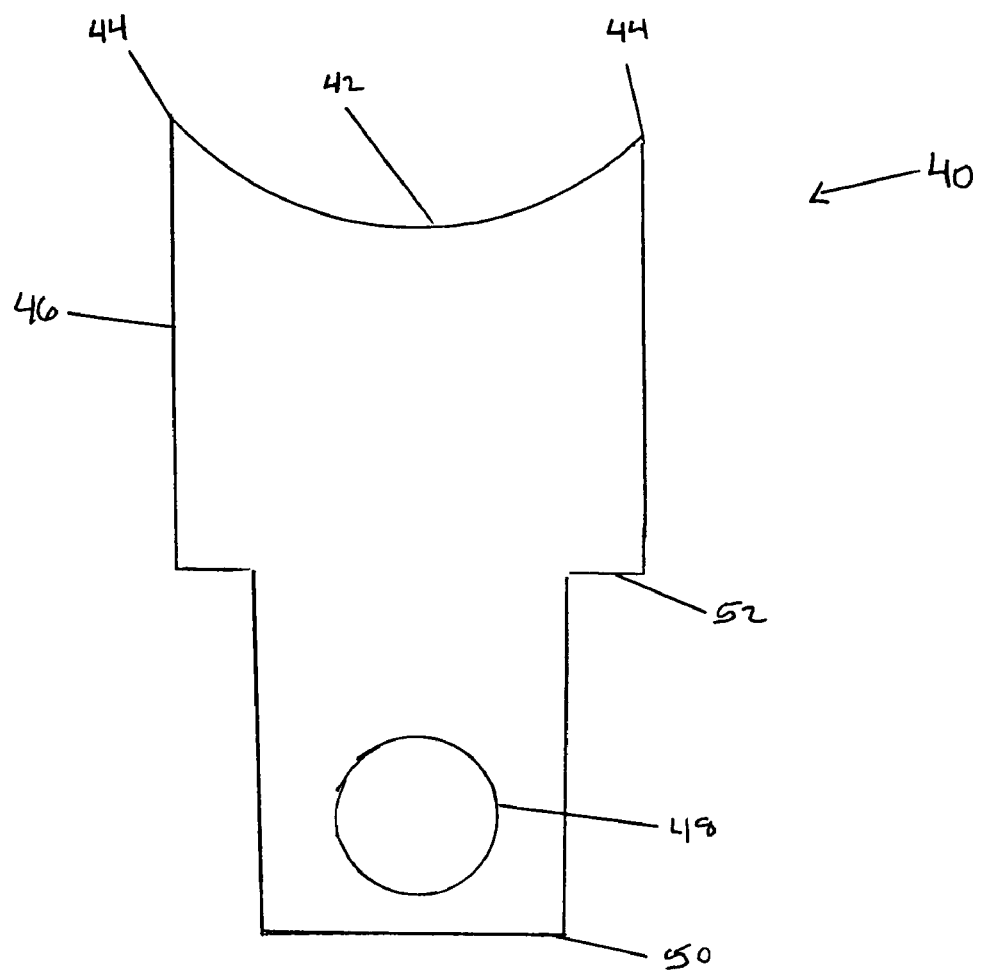
FIG. 3 is an elevational view of a scraper blade of the fuel rod scraping tool of FIG. 1.

Referring to FIG. 3, a blade 40 for a CRUD removal device 10 is illustrated. The blade 40 is provided with a cutting surface to remove and/or dislodge CRUD material from an exterior of the nuclear fuel rod 24. The removed flake material can be gathered to determine the material constituents of the CRUD. The blade 40 has an upper surface wherein a cutting top 44 extends down from a high point in a semicircular arc to a cutting bottom 42. Additionally, the blade 40 extends again from the cutting bottom 42 up to another cutting top 44 completing the arc. The arc is configured such that an exterior edge of a fuel rod 24 may be placed on the blade 40 for removal of CRUD. The blade 40 is configured with sides 46 which extend down from the cutting top 44. The sides 46 may be lengthened or shortened such that the blade 40 is provided with flexibility. The rigidity of the blade 40 may be chosen according to anticipated CRUD deposit sheer strength. The blade 40 is designed to not be rigid when a fuel rod 24 is contacted on the cutting surface thereby allowing superior CRUD removal capability. The sides 46 may be lengthened or shortened based upon the anticipated force to be exerted on the fuel rod 24 during scraping operations, as well as a total thickness of the blade 40. The sides 46 may be reduced in overall width by a width reduction 52 that allows for the required flexibility of the blade 40. The blade 40 may be attached to the housing 12 through a support rod that extends through a support rod hole 48 in the blade 40. The size of the support rod hole 48 may be adjusted such that differing sizes of support rods may be used in conjunction with the blade 40. The support rod hole 48 provides a snug connection between the support rod and the blade 40 to allow the blade 40 to be utilized for scraping operations without the blade 40 becoming dislodged or tilting an excessive amount. A blade bottom 50 is placed on the housing 12 such that the blade bottom 50 contacts the housing 12 thereby preventing rotation of the blade 40 during scraping operations. Although shown as a flat bottom, the blade bottom 50 can be configured in any arrangement that would fit a corresponding bottom of the housing 12.

Figure 4:
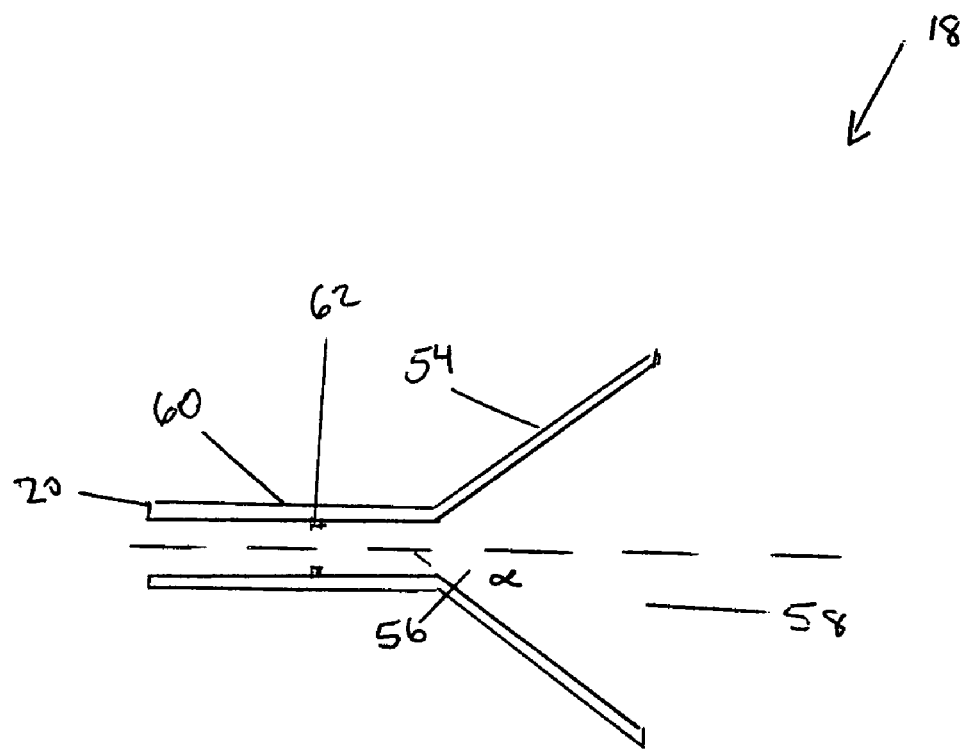
FIG. 4 is a cross-sectional view of a funnel weldment of the scraping tool of FIG. 1.

Referring to FIG. 4, a side cross-sectional view of a funnel weldment 18 is illustrated. The funnel weldment 18 is comprised of a cone 54 which extends from an opening 58 to a exit end 20. The funnel weldment 18 allows a fuel rod 24 to be inserted into the housing 12 through the opening 58 to allow for precise placement of the fuel rod 24 inside the housing 12 during scraping operations. A seal may be placed around the weldment 18 and in the housing 12 to limit material from exiting the housing 12. The exit end 20 may be positioned such that a guide way 60 will direct the fuel rod 24 along a desired pathway in the housing 12. The guide way 60 may be angled such that the guide way 60 snuggly fits around the exterior periphery of the fuel rod 24. The guide way 60 may also be configured with an internal seal 62 to allow the fuel rod 24 to be placed within the funnel weldment 18 such that scraped material will not pass out of the housing 12.

The CRUD scraping tool 10 may be attached to a structure in the fuel pool such that after use, the tool 10 may be removed from the fuel pool environment. The housing 12 may be opened and the scraped particles may be removed for further analysis using a Scanning Electron Microscope described below. The scraping tool 10 may also have a demineralized water intake and outlet such that CRUD material loosened during scraping can be gathered in a filter housing located near or at the outlet of the housing 12.

New Crud Flake Analysis Methodology

A new crud flake analysis methodology has also been developed for BWR and PWR crud using traditional analytical techniques, including SEM/EDS, XRD and ICP/MS. The focus of the evaluation is shifted to CRUD flake analysis from bulk properties to obtain a more clear understanding of crud morphology and spatial distribution of contaminant species. To do so all analysis are done on intact flakes.

Objectives of the CRUD Flake Examinations are the Following:

To physically characterize the CRUD morphology;
To determine the presence, size and shape of crud boiling pockets at the fuel surface;
To determine the presence, size and shape of steam chimneys and capillaries;
To determine overall porosity/density of the deposit;
To provide microscopic EDS elemental analysis inside crud boiling pockets and in other locations of crud situated at the fuel surface;
To attempt to isolate the crud boiling pockets' characteristic morphologic formations for further analysis.

These examinations included Inductively Coupled Plasma (ICP) Spectroscopy for total concentration of common crud/fuel oxide metals, microphotography, X-Ray Diffraction (XRD) to qualitatively identify the major crystalline components in solid bulk samples, scanning electron microscopy (SEM) including energy dispersive spectroscopy (EDS), and porosity and density measurements. All these analyses have been performed up to now for PWR or BWR bulk fuel CRUD, due to the method of sampling and the of CRUD nature on bulk samples SEM/EDS provide qualitative and quantitative analysis, elemental distribution, and surface topography and guides other analyses from an image at high magnification. Also gamma spectroscopy was performed to determine specific bulk activity of crud samples that were analyzed for metals.

There are known disadvantages for all types of the bulk analysis. For example, in XRD: The CRUD transfer consisted of removing manually the deposit from a portion of the filter, transferring the deposit to a vessel with water methanol mixture and manually stirring the solution with a glass wand to suspend in the liquid. The resultant slurry was filtered through a 5 micron filter. The filtered solid was transferred to a glass slide and fixed for X-ray diffraction. The transfer itself was required because the filter material spectra interfered with the crud material spectra.

Another known disadvantage of the present analysis method is that X-Ray Diffraction (XRD) was used to qualitatively identify the major crystalline components in solid samples such as oxides (e.g., magnetite, hematite, alpha-iron, etc.) in bulk samples.

Another known disadvantage is that since the selection of the sample material to be used in the test is random, there is no assurance that the XRD plot obtained truly represents the totality of the sample.

Another known disadvantage of the bulk analysis methods is that the quantity of solid material collected has to be (by flake scraping methods) large to insure an adequate homogeneous mixing of the CRUD sample. That makes it possible that some of the species existing in the CRUD may not be contained or detected in the sample.

Another known disadvantage is that existing trace quantities may not be identified by XRD because of the small sample size. Amorphous phases are not determined by XRD techniques.

Another known disadvantage is that the sensitivity of XRD for a given compound varies with a combination of such factors as density, degree of crystallization, particle size, and coincidence of strong lines from other constituents and the kind and arrangement of the atoms of the components. When a high fraction of iron is present (as with most CRUD deposits), some constituents are difficult to detect because of the high mass absorption coefficient of iron. As a result, the detection sensitivity for these constituents decrease and their limit of detection (LOD) and limit of quantification (LOQ) increase.

XRD is not generally considered a quantitative analysis technique, although relative percentages of compounds detected can be established and characterized as major (greater than 25%), medium (10%–25%), minor (5–10%) and trace (less than 5%) levels. In some cases, calibration curves can be generated using known quantities of one or more species of interest to estimate their percentages in samples to approximately +5%. Minimum sensitivity can be as low as about 0.1 percent.

An additional limitation of bulk techniques as applied today for XRD, SEM/EDS analyses etc. is that the samples have to be pulverized and mixed to obtain adequate spectra for analysis. As a result, important information on CRUD deposit stratification is lost. Because the physical structure of the CRUD is as important, and likely more important, to determining its effect on nuclear fuel performance, the loss of this information is a serious limitation of previously-available analysis techniques.

The discussion above stresses again the fact that for fuel flake analyses, the XRD method provides only an indication of the species existing in the crud. Further confirmatory work must be done through SEM/EDS.

Changes in Preparation of Flakes for SEM/EDS Method to Adapt Itself to In-Situ Analysis of CRUD As part of the CRUD flake analysis, SEM/EDS techniques were modified and refined in order to provide significant data for in-situ analysis. Standard ICP, XRD, and gamma spectroscopy techniques were used to aid in interpreting the SEM/EDS data.

To examine the fuel flakes through in-situ method, special radiological precautions are followed. Some of these samples have large $\beta$ and $\gamma$ radiological fields. Contact with the samples was carefully monitored to control exposure. All activities were conducted under stringent radiological protection methodology. Accidental mishandling of these samples can result in the spread of contamination and creation of hot spots. All work areas were cordoned off while handling these samples and cleaned up immediately after each operation.

The preliminary selection of a flake consisted in selecting from a large number of filtered scrapes identified on a given filter paper the ones that looked larger and sturdier. Many of the large scrape samples may be simple agglomerations of amorphous substance, mostly Hematite. When lightly touched, these agglomerations disintegrate.

Figure 6:
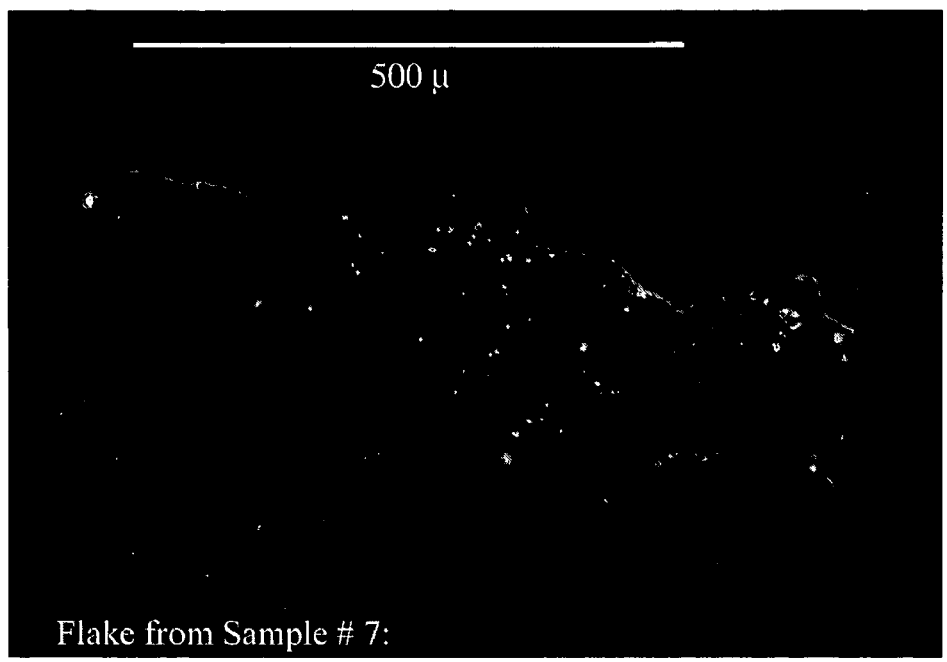
FIG. 6 is a view of an acceptable flake sample before washing.

The scrapes that looked and behaved sturdier were first examined under a microscope to see if the sample could be considered a flake, and how free it was of loose Hematite. FIG. 6 presents a potentially acceptable flake sample, heavily covered with Hematite. If Hematite was attached to the sample, as in the case of FIG. 6, then combinations of successive washings and scrubbings would eventually clean the potential flake sample, as presented in FIG. 8. Note that FIGS. 6 and 7 present the same potential flake sample before and after washing.

Figure 7:
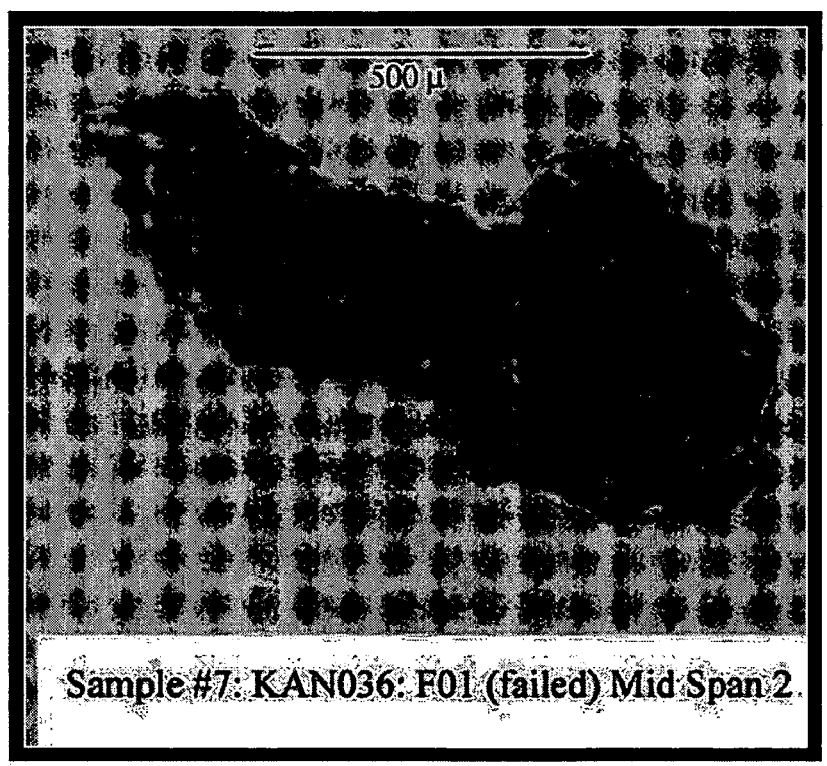
FIG. 7 is a view of an acceptable flake sample after washing.
Figure 8:
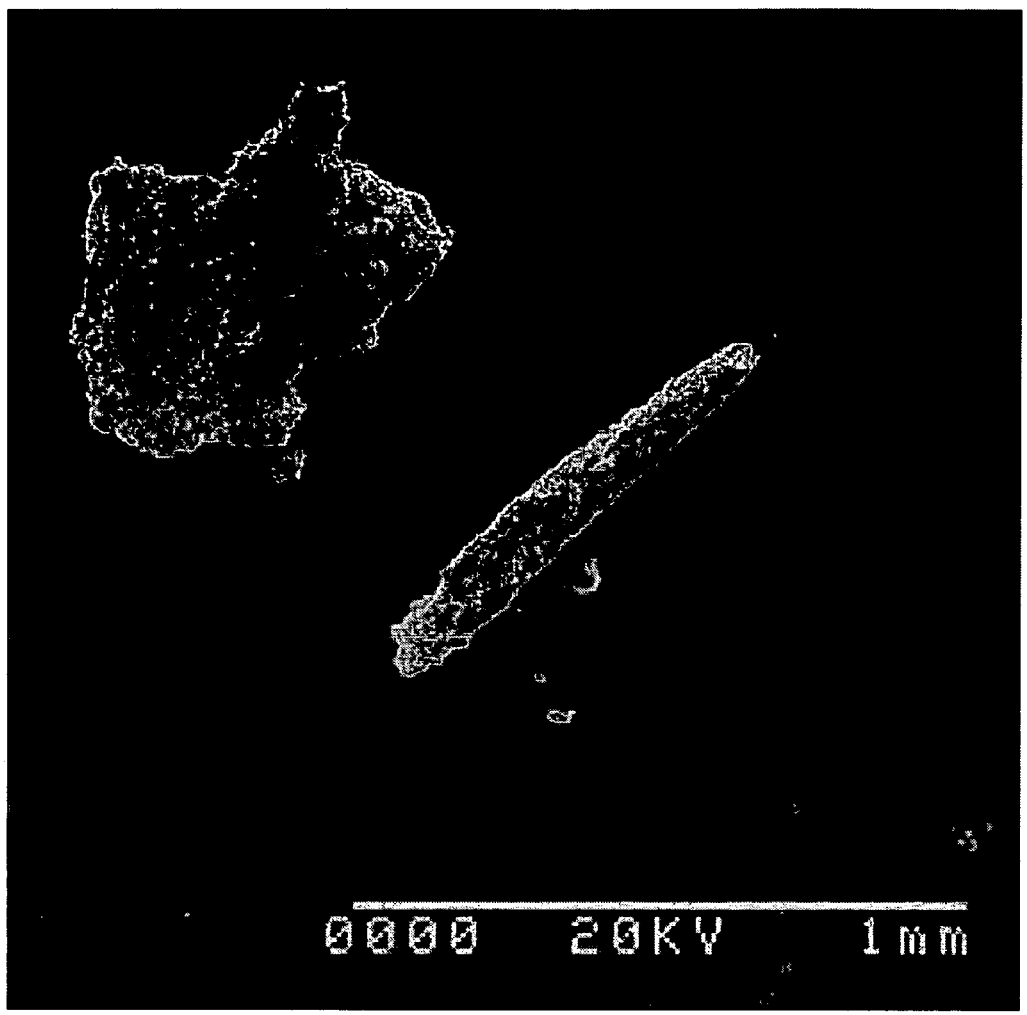
FIG. 8 is a potential flake sample after washing and separation into components.

Successive examinations under a microscope of the potential flake sample of FIG. 7 revealed that the flake actually consists of two flakes (see FIG. 8). One of the samples was mounted vertically and another one horizontally.

The next step in flake sample preparation was the optical examination for orientation, where a number of steps were conducted to allow the positive identification of the ID and the OD of the flake. The steps consisted in taking a series of microphotographs of each side of the sample, observing significant differences and then proceeding to close-up microphotographs. The latter examinations revealed through curvature and smoothness of surfaces if a bona-fide ID (fuel pin side) or OD (fluid side) flake surface had been identified. The process may be by trial and error. Accordingly some of the steps were modified based on initial observation of the condition/type of the subject flake.

Figure 9:
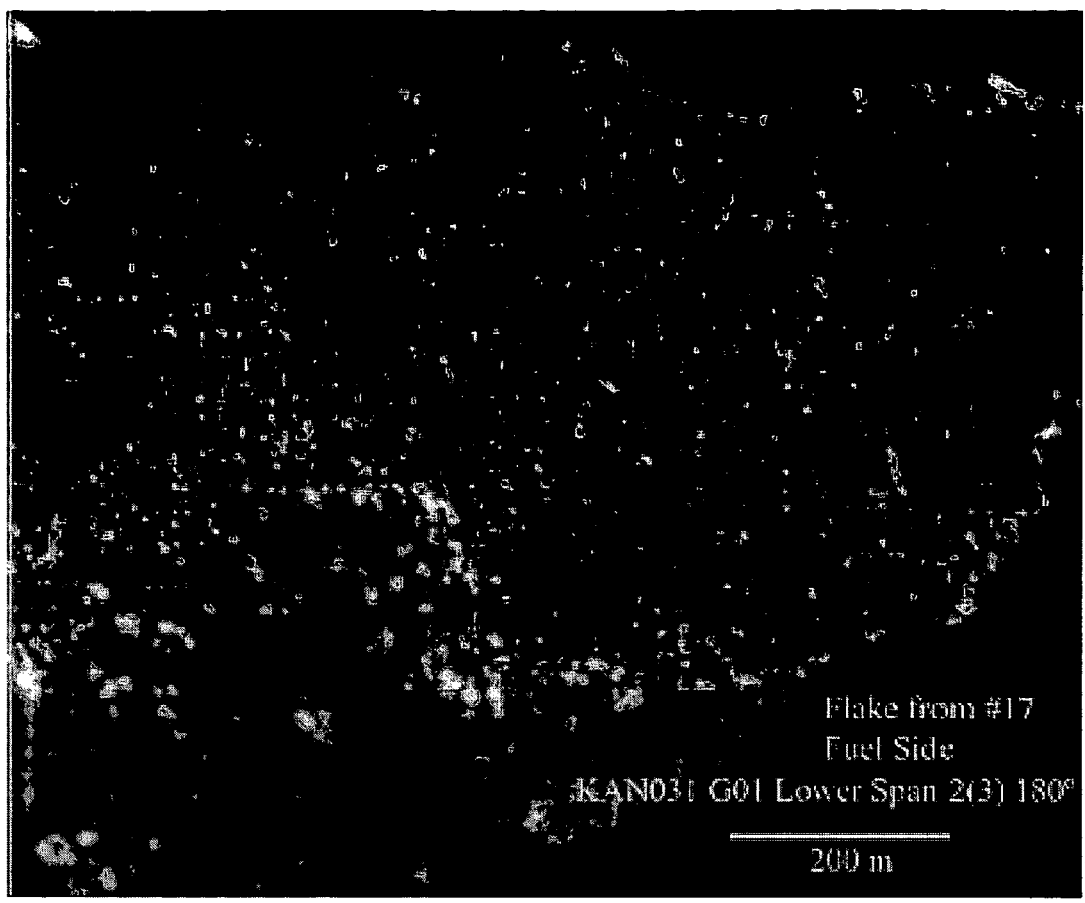
FIG. 9 is a view of a fuel pin face of an acceptable flake sample.
Figure 10:
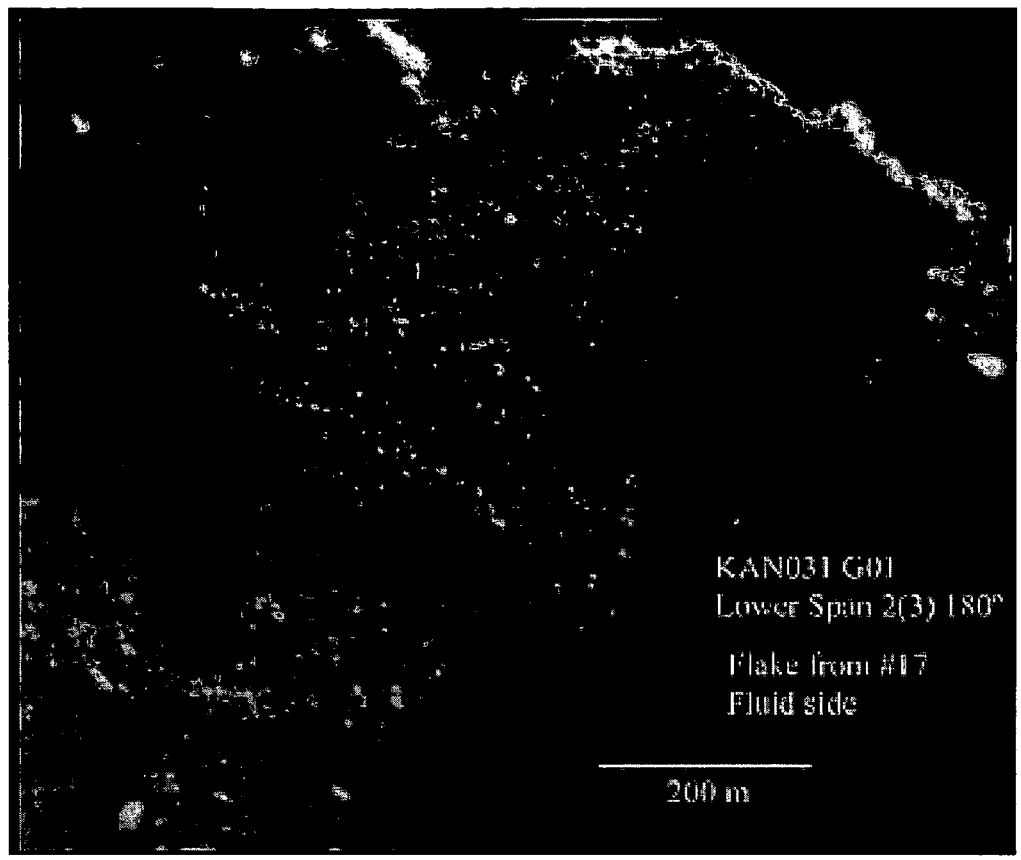
FIG. 10 is a fluid face view of an acceptable flake sample.
Figure 11:
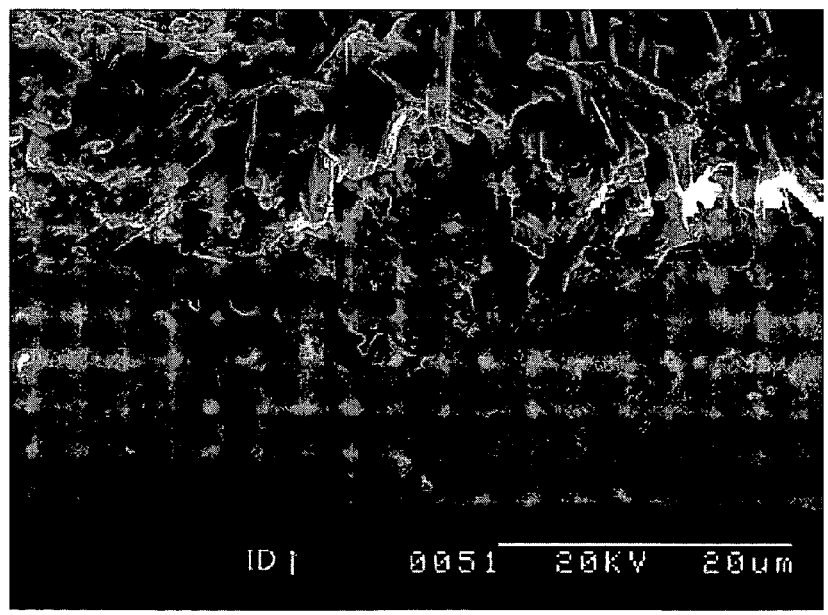
FIG. 11 is a SEM view of a flake sample before tilting the flake relative to an electron beam.
Figure 12:
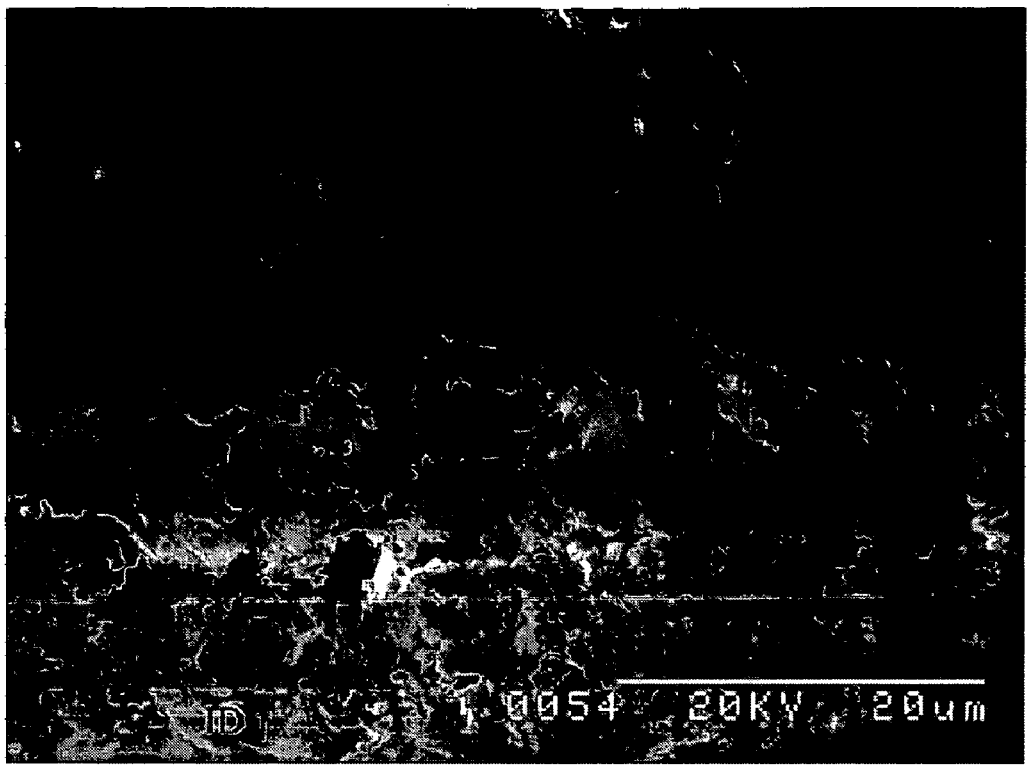
FIG. 12 is a SEM view of a flake after tilting the flake relative to the electron beam.
Figure 13:
FIG. 13 is an elemental map SEM photomicrograph of a flake sample for analysis.
Figure 14:
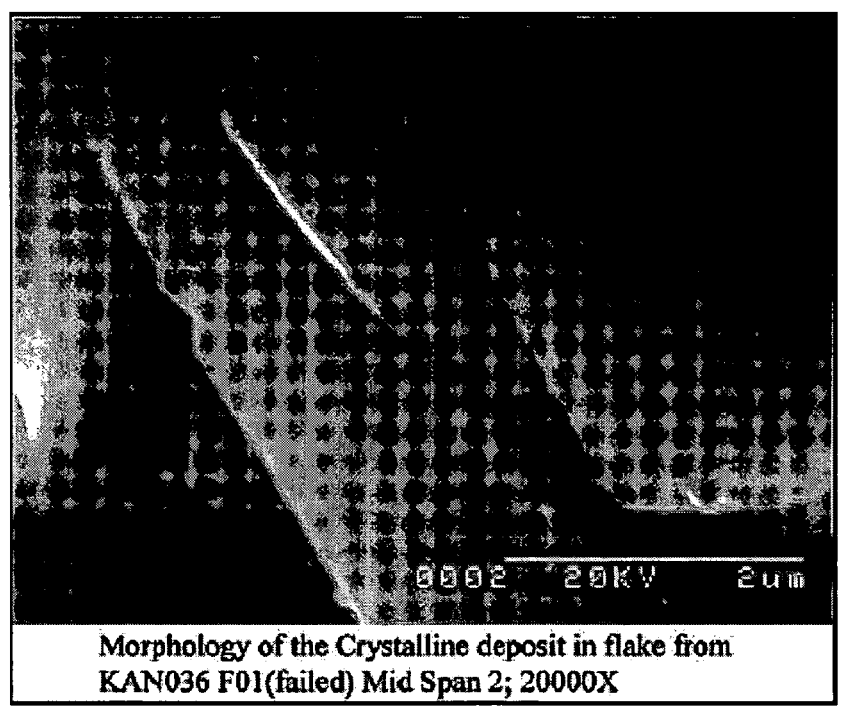
FIG. 14 is a SEM view of a crystalline material in a failed fuel rod flake.

A successful flake would have both the ID of the flake (fuel pin side) and the OD side (fluid side) clearly identified and their features un-modified by previous flake handlings or foreign objects. FIGS. 9 and 10 present a photomicrograph of an acceptable flake sample ID and OD surface. Features on both surfaces are clearly identifiable Modified Scanning Electron Microscopy-Energy Dispersive Spectrometer Analyses FIG. 10 is a fluid face view of an exemplary acceptable flake sample. FIG. 11 is a view of a flake before tilting of the flake with respect to a scanning electron microscope beam. FIG. 12 is a view of a flake after tilting to provide a clearer view. FIG. 13 is an elemental map and SEM photo micrograph of a flake sample. FIG. 14 is a view of a crystalline material in a failed fuel rod.

The modified combination Scanning Electron may be used in Microscope-Energy Dispersive Spectrometer (SEM/EDS) the new flake analysis methodology described herein. It is used in conjunction with the previously-available bulk techniques (ICP, XRD and Gamma Spectroscopy) in order to extrapolate and integrate the critical information of local CRUD characteristics in the assembly of the data from crud.

Due to the small size of fuel crud samples collected, all bulk analyses in the example embodiment (ICP, XRD and Gamma Spectroscopy) have a high degree of uncertainty. Both the sensitivity of the techniques, as well as the randomness of the samples collected is negatively impacted if the quantity of the CRUD collected is very small.

SEM uses a finely focused electron beam to form an image at high magnifications (up to 20,000× in the present work) with virtually unlimited depth of field. The electron beam generates secondary electrons, backscattered electrons, and characteristic X-rays as it is scanned across the surface of the sample. The secondary and backscattered electrons are used to form viewable images of the sample creating very accurate surface topography images of features only a few nanometers (nm) across. In some instances, in the present work, features no bigger than 200 nanometers had to be identified in the crystalline make-up of portions of crud deposit. Function of the bulk conductivity of the CRUD. As the SEM image magnification increases, depending on the bulk conductivity of the CRUD, surface charging can occur. This has at times limited the achievable magnification in regions of interest.

With the attachment of an energy dispersive spectrometer (EDS) to the SEM, the chemical analysis (microanalysis) of the CRUD flake sample was performed by measuring the energy or wavelength and intensity distribution of X-ray signal generated by a focused electron beam on the specimen. The advantage of using the SEM/EDS combination for small flake analyses was that very precise and accurate chemical analyses (relative error 1–2%) can be obtained from areas of the solid no larger than 0.5–3 micrometer diameter. This is important for the credibility of crevice analyses performed on CRUD flakes to evaluate specific local conditions.

Yet another attachment to the SEM, which is the electron backscattered pattern (EBSP) apparatus and method, can be used to successfully determine the crystal system, lattice parameters of the unit cells and point accordingly towards the group of the crystals belonging to an in-situ specific portion (crevice) of the flake.

The methodology of SEM/EDS analysis for each of the individual flakes was modified by special flake specimen preparation (identification of adequate sample, cleaning of tramp material, mounting of the delicate specimens, and careful exposure of "pristine" surfaces for investigation). A summary of the developed methodology analysis follows (the preparation being described previously).

SEM Examination of Fuel and Fluid Side of Flake

The fuel side and the fluid side of the flake were examined at low magnification to find a reasonably flat area. The area was magnified and an EDS and elemental map at magnifications of 100–1000× were taken. Specific features of the area were identified in each case, which appeared as a crevice, crack or hole on that flat area. High magnification micrographs of features (showing the morphology) which have the largest volume (either large diameter and/or depth of the feature) were taken. An EDS and elemental map of two of the largest features were performed. The flatness near the observed feature was analyzed such as to select enough flat surfaces to form a reference plane. Stereoscopic images were taken when possible for further evaluation.

SEM Examination of the Edge of Flake

The correctness and accuracy of the SEM/EDS examination of the edge of a flake depended on whether a good clean break edge was available or could be created.

The edge resulting from splitting the flake at a weak point is rich in features, so, in the example provided, the flake has to be mounted such as to reflect its unique characteristics. In many cases successive mountings were performed until the flake was successfully positioned. The edge area of the flake was examined at low magnifications for a smooth/flat area. EDS and elemental map at magnifications of 500–1000 where taken. Specific features of the edge of the flake such as crevices, steam channels, and capillaries were identified. High magnification micrographs of features (showing the morphology) having the largest volume were taken to support future development of BWR fuel crud model development.

The principle of method for cross-section analysis consists in correlating the SEM/EDS elemental distributions at various locations of the cross-section of the CRUD to follow the depletion in Fe and enrichment in Zn and Si in particular, i.e., individual, crystals and to correlate this chemical information with the size and morphology of the crystals, as well as with their crystallography.

In order to more accurately analyze flakes, a method of measuring the percent void area as a measure of porosity was developed.

In the present example, it was quite difficult to obtain good SEM data from the fuel pin side of the flake due to its slope. The flake, however, was tilted to get the best view of fuel pin side (FIG. 12). As a remedy the sample is tilted until the best view is obtained.

Yet another application of tilting is to correlate SEM images of individual crystals and EDXS spectra from the same crystals using a small probe, i.e., in the spot mode, so the chemistry can be correlated with the size/morphology of individual crystals. This may require tilting the crystals in the SEM to investigate crystal morphology, i.e., to see if they have square or hexagonal shapes and therefore 4-fold (cubic or tetragonal crystal systems) or 6-fold (hexagonal crystal systems) rotation axes.

Tilting of a crud samples of very small size (microns in diameter) can be done using special props or simple glue for example.

There are several advantages of in-situ method to identify phenomena not seen before using classical methods. These include:

a) Identifying crystalline structures at their place of formation in CRUD and comparing them with catalog formation. Advanced localized crystal analysis using SAED or other methods of small area electron diffraction techniques may also be performed.

As an example, copper can be identified in-situ in a separate agglomeration within a crystal matrix containing only zinc and silica. This observation is possible through elemental mapping and photomicrographs of discrete CRUD flakes and EDS analysis at 20,000× of the same area.

The morphology of the crystals can be further compared with known crystals. In our example plan/micrograph a crystal formation with the mineral crystal Willemite may be shown. Willemite is a neosilicate (Zinc Silicate $Zn_2SiO_4$) formed by linking individual silica tetrahedra through positively charged zinc ions in elongated hexagonal prisms crystals. The identification of these types of crystal formation are important in evaluating nuclear plant water chemistry as it affects CRUD formation and transformation during nuclear plant operation.

Although the visual resemblance of crystals is striking, definitive crystal identification needs the exact crystalline phases of the crystal. This may be done in combination with individual crystal elemental analysis, preformed through small area electron diffraction (SAED). The advantage in analyzing flakes is that it allows in-situ SAED, which can lead to a much better understanding of both crevice and steam chimney phenomena.

b) Observing and understanding the coexistence between the minority crystalline structure and the majority compact structure as happens in most CRUD deposits.

The OD side of the flake cross section locations indicates such a case, explaining how silica crystals or silicates incorporates in CRUD deposit.

Figure 15:
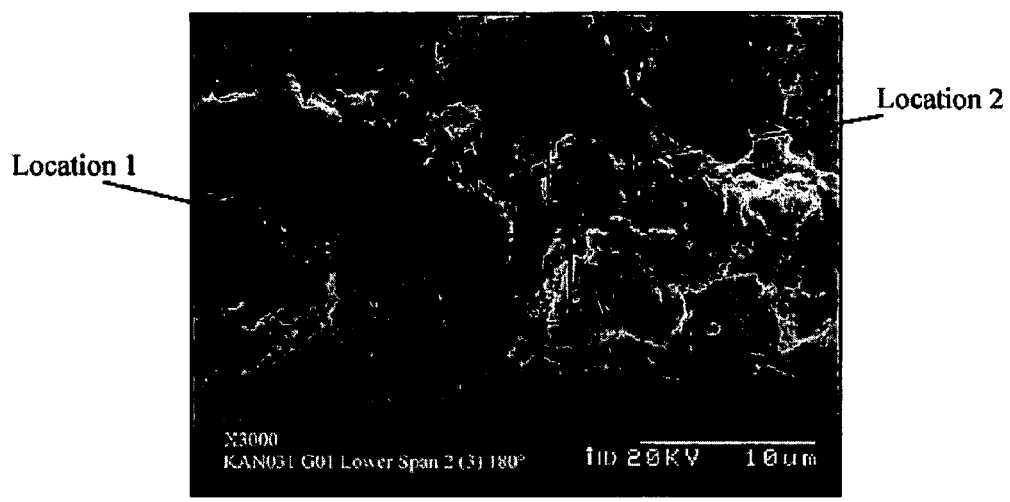
FIG. 15 is a SEM view of an IO side of a flake cross-section at 3000×.
Figure 16:
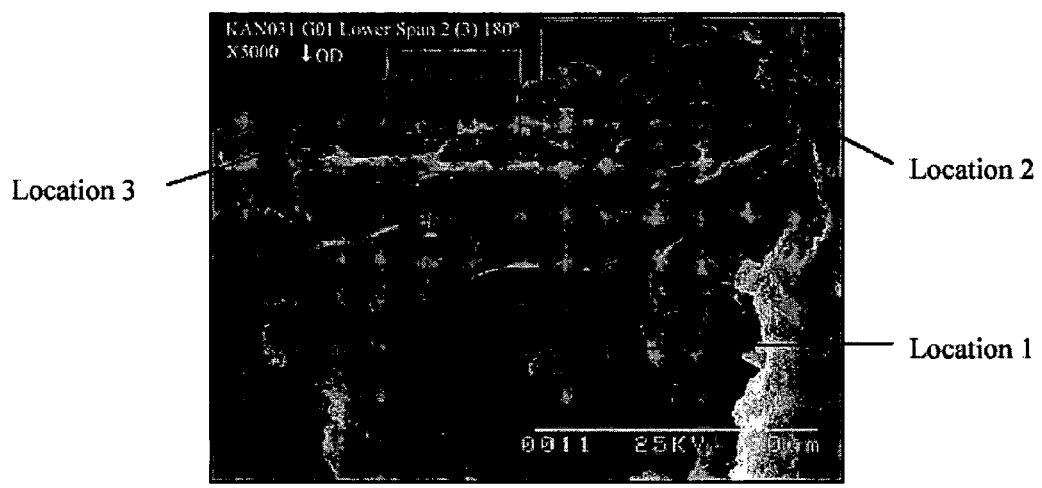
FIG. 16 is a SEM view of an OD side of a flake cross-section at 5000×.

The flake edge OD and ID locations are where high magnification examinations are most beneficial in identifying internal CRUD characteristics. Location #1 in FIG. 15 is the 3000× microphotograph of the upper part of an fuel pin side crevice and the beginning part of a steam chimney. Location #2 in FIG. 15 is an intermediary steam chamber somewhere on a steam chimney. This type of analysis resolution allows an assessment of the elements contributing to deposition on the walls of such an intermediary steam chamber. All three locations in FIG. 16 (a 5000× microphotograph of the fluid side of a CRUD flake cross-section) potentially explain the mechanism of silica crystal incorporation into the deposit.

There are some impediments connected with the relative "large" size of the flake and subsequently the relatively large radioactivity obtained from the flake, which affects the EDS and microphotograph quality at high magnification. The strong gamma emissions by the flake samples can "blind" the SEM/EDS detector and/or skew the EDS results. A method to compensate for this effect was developed and is given below.

The X-ray "glow" in-situ treatment of the sample was recorded. From this information, it was apparent that the high intensity X-ray emission due to decay of $^{55}Fe$ and $^{65}Zn$ (among other species) of CRUD flakes will slightly bias the EDS data evaluation. In this case, the results of the EDS spectra have been adjusted in order to present a realistic assessment of the flake composition. Other elements can show such a "glow" as to preclude their analysis.

c) Observation of Unique Phenomena-Insertion of Structures from Bulk into the Loose Surface Crud.

Figure 17:
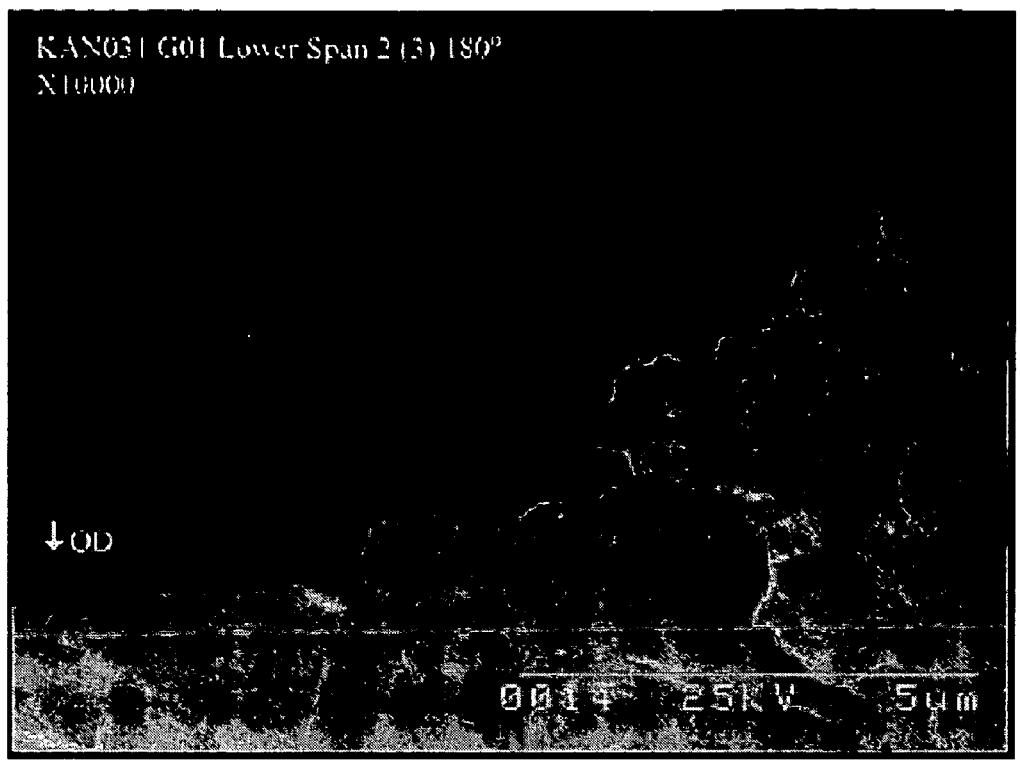
FIG. 17 is a SEM view of the lower span cross-section OD of a flake.

FIG. 17 presents a microphotograph of location #1 on the OD side of a CRUD flake. Here two crystals of chain silicates, needle-shaped structures approximately 0.2 µm in diameter and most likely formed in the bulk water, are seen inserted by the flow in the loose surface crud.

In the foregoing specification, the invention has been described with reference to specific exemplary embodiments thereof. It will, however, be evident that various modifications and changes may be made there and too without departing from the broader spirit and scope of the invention as set forth in the appended claims. The specification and drawings are accordingly to be regarded as in and illustrative rather than a restricted sense.

Flake Porosity and Density

For flaked particles, there is a correlation between the values of density and porosity, wherein if one of the values of density or porosity is known, the other value may be calculated. When both density and porosity are measured, an error correlation for the measuring methodologies may also be determined. For flakes from nuclear fuel rods, however, density measurements of relatively small CRUD particles cannot be accomplished due to the small number of particles obtainable from each rod. Additionally, traditional porosity measurement methods cannot be used due to the extremely small volume for the flake samples. The present invention alleviates these limitations because flake porosity is estimated based on a Scanning Electron Microscope (SEM) image of a flake. The method of calculating porosity using an SEM is accomplished by initially calibrating visual data obtained by the SEM on reference material to establish a density measurement for of the reference material. Errors between measured and calculated valves are expressed as a percentage difference between average porosity determined from direct density measurements, via "solid density", and a calculated average porosity that is obtained by averaging SEM image determined porosities in various locations of the flake cross section. "Solid density" is defined as a sample density which used our assumed atomic composition. This allows the establishment of a reference point, with elements present in a sample sharing 100% of the volume of that sample.

A typical SEM image is produced when the SEM ion beam is rastered across a sample surface. As the ion beam interacts with the sample surface, an emission of secondary electrons occurs from the surface. These emitted electrons are detected by the SEM that has a detector to record these electron emissions. When the electrons strike a topographically elevated portion of a CRUD sample, a greater percentage of the ion beam energy is transferred to the emitted secondary electrons. These secondary electrons carrying more energy are detected by the SEM as these electrons give a stronger secondary electron signal. The SEM then interprets the elevated energy of these secondary electrons as a topographically high area.

As the SEM electron beam is rastered across the CRUD sample, an image containing many discrete pixels, is produced. Each pixel corresponds to one discrete location at which the ion beam was focused and the brightness of each pixel is proportional to the topographical height of the sample at that location. The lighter (i.e., white) pixels represent the "high" elevations, while the darker pixels represent the "low" elevations.

Calibration Method

SEM micrograph images have a distribution of high (light) and low (dark) areas. SEM micrograph images, however, may be skewed toward a lighter shade (i.e., there are no black areas or a lower shade). This skewing or "offset" of SEM images varies from image to image.

In order to normalize the SEM image contrast (distribution between darkest and lightest points), the SEM image is adjusted by setting the darkest points to be pure black and the lightest points to be pure white. This adjustment "calibrates" the contrast of the image to the particular topographical distribution of the sample. Once an image has been properly calibrated, it is possible to use the calibrated image for porosity measurements. In order to perform porosity measurements using SEM images, it is necessary to calibrate the image data using previously measured density values.

To make a direct (empirical) density measurement, at least one CRUD flake is required to have a sufficient mass for weighing. After weighing the flake, an area of a representative side of the at least one flake is calculated from information provided by the SEM image. An edge image of the flake is also obtained, allowing the calculation of a uniform thickness for the flake. An average width of the flake is then estimated using this data. Assuming that the flake is uniform in thickness across all its area, the volume of the flake is next calculated. Next, the density of the flake is calculated as follows:

MeasuredDensity=Weight/Volume

To determine the porosity, the "solid density" of the flake is calculated. The calculation method for the "solid density" utilizes the atomic composition provided by the SEM analysis. Using the atomic composition data, the normalized molar composition is calculated based on an assumed compound mix. Additionally, an average density contribution of each element and total average solid density is calculated.

The relationship between solid density and porosity is:

$$\text{Porosity} = \left(1 - \frac{MeasuredDensity}{SolidDensity}\right) * 100$$
$$= \frac{VoidVolumeDensity}{SolidDensity} * 100[\%]$$

For an infinitesimally small unit depth, porosity can be expressed as a function of surfaces as:

$$\text{Porosity} = \frac{VoidSurface}{TotalSurface} * 100[\%]$$

The next step of the porosity measurement method is to establish a virtual plane, wherein cutting the flake SEM image would result in a porosity expressed as a function of void surface of the total normalized SEM surface for the above determined porosity. A "baseline" grayscale value for all pixels is determined, where values less than or equal to the baseline grayscale value account for an approximate percentage porosity of the total image pixels of the SEM image.

Figure 5:
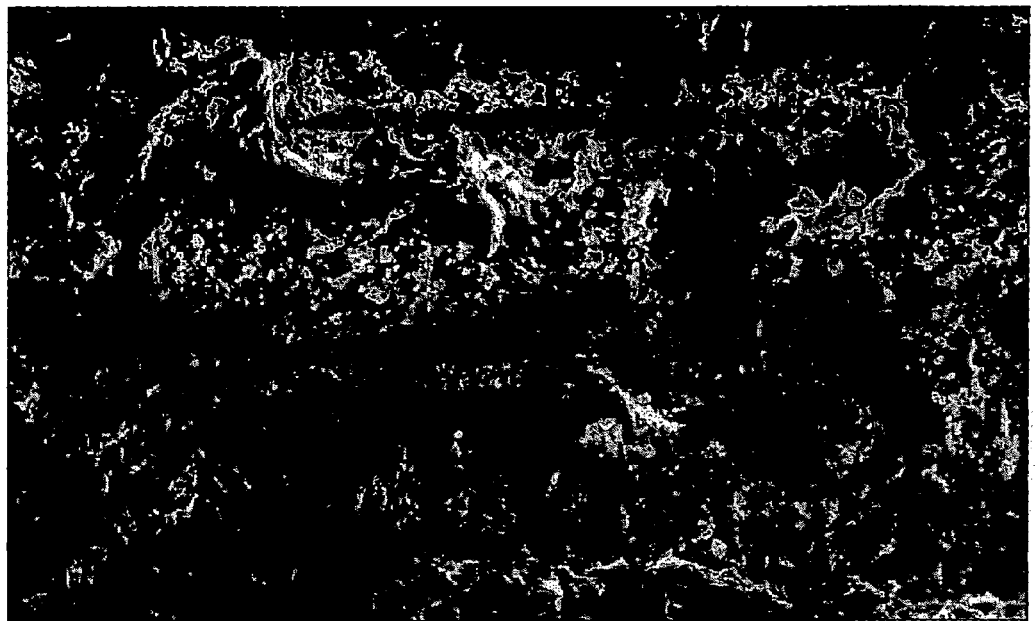
FIG. 5 is a scanning electron microscope view of a boiling water reactor CRUD flake used during porosity calibrations.
Figure 5:
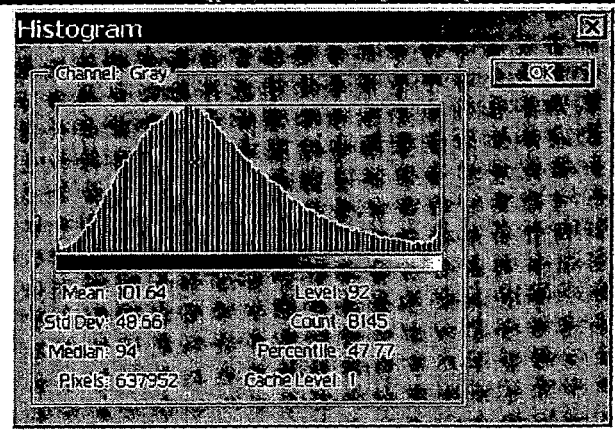

In the exemplary embodiment as provided in FIG. 5, a flake with a porosity of 47.77% is illustrated, the baseline grayscale of the SEM image is measured as a 92 value, for which 47.77% of the pixels are darker than or equal to the grayscale value. The maximum grayscale value is, for example, 255. For a material with high porosity, the material will have a larger number of points close to a "0" position, because the material has many more crevices (values under the average grayscale value 92). In the case of a less porous material, the number of points close to 0 would be reduced, and the number of points close to "255" position larger.

Measurement Results

Using this method, the porosity of other CRUD flakes may be estimated. In sample analysis performed, it has been determined that CRUD may be much denser in failed regions of nuclear fuel rods that unfailed regions. It has also been determined that there is an error band for the average computed data compared with the average measured data of approximately +/−14.5%.

The following principle steps are performed using the methodology presented above:

1. Crop the SEM image to eliminate any labels that may affect the results.
2. Adjust the contrast of the SEM image such that the darkest points are pure black and the lightest points are pure white.
3. Determine the density of at least one flake sample through empirical measurement and through the "solid density" concept for the porosity of that sample.
4. Determine for that sample the percent of pixels that have a grayscale value equivalent to the porosity as determined from empirical density data.
5. Apply the grayscale equivalent to the rest of flake sample cross sections.
6. The percentile of pixels that are darker or equal to that grayscale value is equal to the approximate porosity of the sample.
7. From porosity values, the density of a flake results wherein the porosity and the solid density are used to determine the density of the flake sample.

Table 1 presents an example calculation of a solid density for a hypothetical CRUD flake sample.

TABLE I

| Element | Atom % | Assumed Compound | Mol % | Normalized Mol % | Theoretical Density (g/cc) | Avg Density Contribution (g/cc) |
|---|---|---|---|---|---|---|
| Mg | 2.58 | $MgSiO_3$ | 2.58 | 3.3 | 3.19 | 0.10 |
| Al | 2.4 | $Al_2SiO_5$ | 1.2 | 1.5 | 3.145 | 0.05 |
| Si | 19.39 | $SiO_2$ | 13.7 | 17.3 | 2.334 | 0.40 |
| P | 0.86 | P | 0.86 | 1.1 | 1.823 | 0.02 |
| Ca | 0.29 | $CaSiO_3$ | 0.29 | 0.4 | 2.92 | 0.01 |
| Cr | 1.23 | $CrO_2$ | 1.23 | 1.6 | 4.89 | 0.08 |
| Mn | 1.62 | $MnSiO_3$ | 1.62 | 2.0 | 3.48 | 0.07 |
| Fe | 27.75 | $Fe_2O_3$ | 13.875 | 17.5 | 5.25 | 0.92 |
| Cu | 12.85 | CuO | 12.85 | 16.2 | 6.31 | 1.02 |
| Zn | 31.04 | ZnO | 31.04 | 39.2 | 5.6 | 2.19 |
| SUM | 100.01 | | 79.245 | 100.0 | Average Density (g/cc) | 4.87 |

Note: Calculation performed for Exemplary Flake using EDS atomic % values

Table 2 presents an idealized porosity calculation for a hypothetical CRUD flake sample provided in Table 1.

TABLE 2

| | Flake A (Sample #7) | Flake B (Sample #17) | Flake D (Sample #18) |
|---|---|---|---|
| Flake Average Measured Porosity (%) | N/A | 47 | N/A |
| Flake Average Computed Porosity (%) | 32.5 | 55 | 58 |
| Flake Edge OD Side Measured Porosity (%) | | 41 | 48 |
| Flake Edge Middle Side Measured Porosity (%) | 40 | 44 | 43 |
| Flake Edge ID Side Measured Porosity (%) | 25 | 80 | 84 |

*An error band of +/−14.5% should be considered between average measured and average computed porosity. The measured porosity has been obtained from empirically measured flake density.

Table 3 presents an exemplary calculation for denoting based on SEM Images.

TABLE 3

| | Flake A (Sample #7) | Flake B (Sample #17) | Flake D (Sample #18) |
|---|---|---|---|
| Flake Measured Density (g/cc) | N/A | 2.56 | N/A |
| Flake Average Computed Density (g/cc) | 3.79 | 2.19 | 2.00 |
| Flake Edge OD Side Computed Density (g/cc) | | 2.87 | 2.50 |
| Flake Edge Middle Side Density (g/cc) | 3.37 | 2.73 | 2.74 |
| Flake Edge ID Side Computed Density (g/cc) | 4.21 | 0.97 | 0.77 |

• An error band of +/−14.5% should be considered between flake measured and flake average computed density.

What is claimed is:

1. A method for analysis of a CRUD flake cross section on a nuclear fuel rod, comprising:
    determining a morphology of crystals of the flake;
    determining a size of the crystals of the flake;
    correlating elemental distributions of the flake at various locations on the flake, wherein the distributions are obtained with a scanning electron microscope with attached energy dispersive spectrometer;
    determining chemical elements including depletion of iron and/or an enrichment in zinc and silicon in the crystals by the elemental distributions; and
    correlating the depletion of iron and the enrichment in zinc and silicon with the size and the morphology of the crystals.

2. The method according to claim 1, further comprising:
    tilting the flake with respect to a beam from the scanning electron microscope.

3. The method according to claim 1, further comprising:
    obtaining EDXS spectra of individual crystals; and
    tilting the crystals relative to a beam of the SEM to investigate crystal morphology.

4. The method according to claim 3, wherein the tilting is done using one of many possible props and/or glue.

5. The method according to claim 1, further comprising:
    performing a small area electron diffraction on the crystals.

6. The method to perform an analysis of CRUD on a nuclear fuel rod according to claim 1, wherein the step of analyzing the CRUD comprises:
    cropping a scanning electron microscope image;
    adjusting a contrast of the image such that darkest points of the image are pure black and lightest points are pure white;
    determining a density of at least one flake reference sample;
    determining a percent of pixels that have a grayscale value equivalent to porosity determined from the density;
    applying a grayscale equivalent to a remainder of flake samples;
    determining a percentage of pixels that are one of darker and equal to the grayscale value to determine a porosity; and
    determining a density of the remainder of the flake sample based on the porosity.

* * * * *